United States Patent [19]

Barraclough

[11] 3,930,761
[45] Jan. 6, 1976

[54] PORTABLE AND MANUALLY OPERABLE PERISTALTIC PUMP

[75] Inventor: Keith S. Barraclough, Basingstoke, England

[73] Assignee: The Boots Company, Ltd., Nottingham, England

[22] Filed: Dec. 19, 1972

[21] Appl. No.: 316,589

[52] U.S. Cl. .................. 417/476; 128/215; 222/79
[51] Int. Cl.² ............... F04B 43/08; A63H 3/18; A61M 5/00
[58] Field of Search ............ 417/476; 128/215, 216, 128/223, 218 R; 222/79, 210, 214

[56] References Cited
UNITED STATES PATENTS

| 401,950 | 8/1889 | Hausmann | 417/476 |
| 424,944 | 4/1890 | Allen | 417/476 |
| 2,527,614 | 10/1950 | Arpin | 222/79 |
| 3,318,482 | 5/1967 | Voce | 222/79 |
| 3,353,537 | 11/1967 | Knox | 128/218 R |
| 3,649,138 | 3/1972 | Clay | 417/477 |
| 3,674,024 | 7/1972 | Cirillo | 222/79 X |
| 3,786,683 | 1/1974 | Berman et al. | 417/476 X |

FOREIGN PATENTS OR APPLICATIONS

| 11,975 | 8/1933 | Australia | 222/79 |
| 948,312 | 1/1949 | France | 222/79 |
| 1,246,644 | 10/1960 | France | 417/476 |

Primary Examiner—C. J. Husar
Assistant Examiner—Richard E. Gluck
Attorney, Agent, or Firm—Hammond & Littell

[57] ABSTRACT

A peristaltic pump comprising a portable housing capable of being held in the hand and which carries means defining an elongated surface, a tube leading past the housing in contact with the elongated surface that includes near one end of the housing, a non-return valve that allows fluid to flow only in the direction that leads away from the housing, the tube being a flexible tube along at least that part of its length in contact with the elongated surface, a roller which is reciprocable along the flexible tube, means for squeezing the tube against the surface by the roller and thereby closing the tube and for moving the roller along the tube towards the non-return valve while thus squeezing the tube, means for continuously biasing the roller away from the non-return valve and means to withdraw the roller from said tube during or subsequent to its return to its initial position whereby the flexible tube returns substantially to its normal configuration.

1 Claim, 3 Drawing Figures

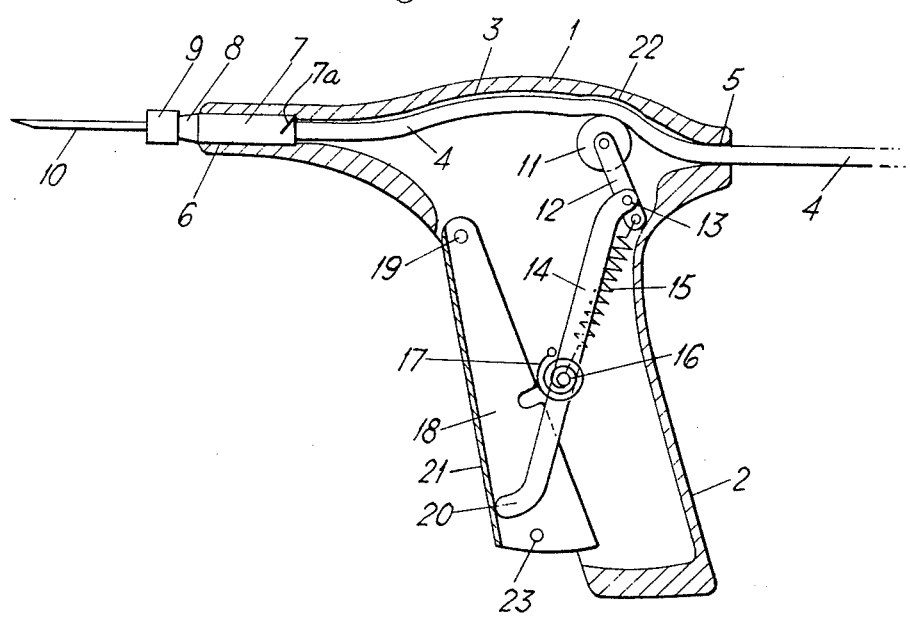
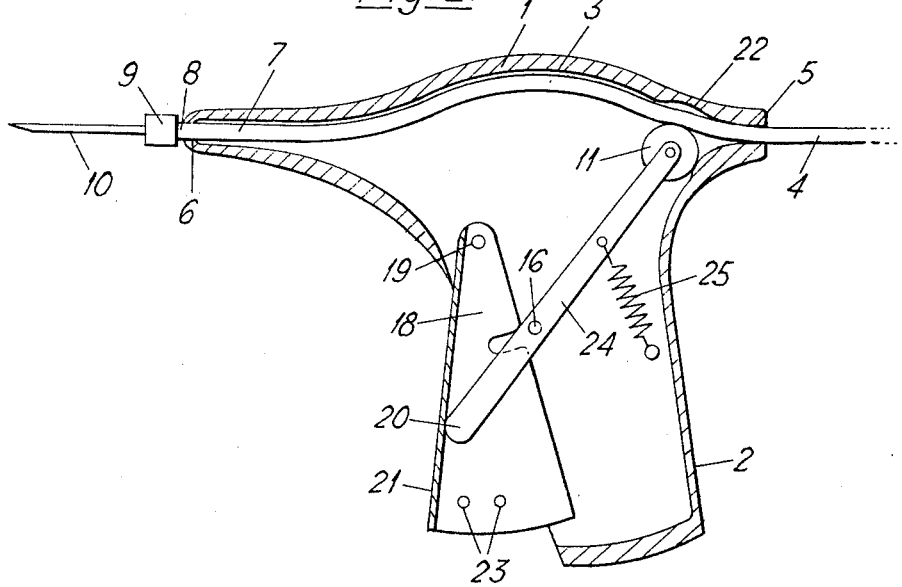

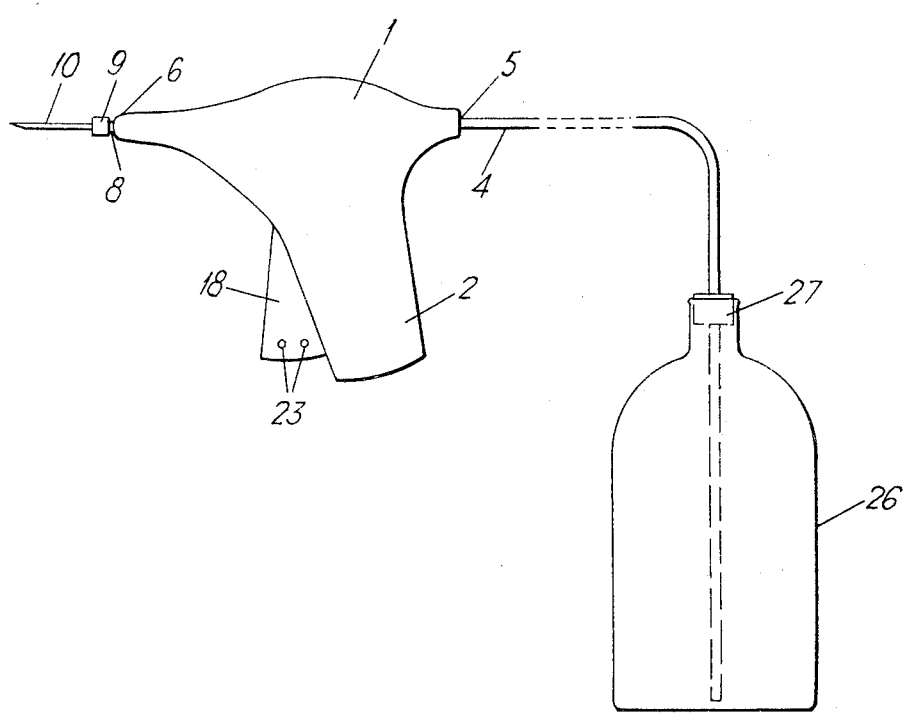

PORTABLE AND MANUALLY OPERABLE PERISTALTIC PUMP

This invention relates to a portable and manually operable pump by which liquid can be dispensed in predetermined amounts by manual operation of the pump, and in particular it relates to pumps that can be used for vaccination of living bodies, including both humans and animals.

Vaccination pumps generally comprise, for example, a simple syringe having a piston that moves through a cylinder to expel liquid from the cylinder. However it is also known, for example from U.S. Pat. No. 1,961,489, to include the liquid to be injected in a flexible cylindrical container and then to press a flat surface against one side of the container so as to expel the liquid from the container.

Peristaltic pumps are well known and are usually designed for supplying continuously a continuous feed of liquid. Thus liquid may be led to a resilient tube and a series of rollers may pass along the tube while squeezing it against a backing surface and thereby peristaltically forcing the liquid through the tube. These pumps are usually fairly complicated and are neither conveniently portable nor conveniently manually operable.

A peristaltic pump according to the invention comprises a portable housing capable of being held in the hand and which includes or carries means defining an elongated surface, a tube leading over or through the housing along the elongated surface and that includes, at or near one end of the housing, a non-return valve that allows fluid to flow only in the direction that leads away from the housing, the tube being a flexible tube along at least that part of its length that leads over the elongated surface, a roller which is reciprocable along the flexible tube, and means for squeezing the tube against the surface by the roller and thereby closing the tube and for moving the roller along the tube towards the non-return valve while thus squeezing the tube.

Generally the pump contains just one roller, unlike conventional peristaltic pumps where there are usually several rollers.

The particular advantage of the pump according to the invention is that it can conveniently be used for vaccination of humans or animals and thus in use will have an injection needle outside the housing fitted to the tube at or near the non-return valve.

The pump is also useful for delivering doses of a variety of other liquids, e.g., as jets or sprays. Thus in place of having a needle it may be fitted with a nozzle, designed to give a spray or jet. The injection needle or nozzle may be permanently fitted, and may even be moulded with the tube, or may be replaceable. Unless the needle or nozzle is moulded with the tube then the tube will terminate at or near the non-return valve in a fitting in which the needle or nozzle may be fitted, either permanently or replaceably.

Liquid may be supplied to the tube, for peristaltic pumping along the tube and through the non-return valve, from any convenient source, the end of the tube distant from the non-return valve extending into the source. Usually the source of liquid is outside the housing. Thus, for example, the tube may lead to a reservoir for liquid. For example in veterinary use the operative may carry a flexible reservoir and the tube may lead from this to the pump, which the operative will hold in his hand. Conveniently the reservoir is a sealed flexible reservoir that collapses as liquid is pumped out of it.

An essential characteristic of the invention is that as the roller moves along the tube it shall squeeze the tube against a backing surface sufficient that during the travel of the roller the tube is closed, whereby peristaltic pumping occurs. As a result the backing surface must be sufficiently elongated to serve as a backing surface over the desired travel of the roller. In practice it must also be fairly smooth, in order that the tube is closed as the roller moves along it. Of course if desired the surface can be ribbed or ridged provided the ribs are not so deep as to prevent closing of the tube. The means defining the elongated surface can be, for example, a second roller that moves with the first and against which the first roller presses the tube, but most usually the housing includes or carries the elongated surface.

The elongated surface may be outside the housing in which event the tube will be outside the housing. Thus the roller pair may be outside the housing or a surface outside the housing, e.g. an outside surface of the housing, may serve as the elongated surface. Usually however the elongated surface and the tube are inside the housing. For example the surface may be an inside surface of the housing.

By choosing appropriately the length of travel of the roller along the tube towards the valve so one controls the dose of liquid pumped through the valve, and hence through any needle fitted to the tube. In order that the dose can be selected for any particular operation it is preferred that the pump should include adjustable stop means capable of being adjusted to limit the travel of the roller to a predetermined amount.

After the roller has followed its maximum travel towards the non-return valve, and the desired dose or doses have been expelled, it is necessary that the roller should return to a position distant from the non-return valve, ready for the next pumping operation. The pump therefore conveniently includes means for continuously biasing the roller away from the non-return valve, the biasing means usually being a spring.

It is necessary that after the desired dose or doses of liquid have been ejected through the valve and the roller has returned to its rest position that liquid can flow back into the tube, ready for ejection upon the next operation of the pump. Accordingly the roller must not squeeze and close the tube continuously. When the elongated surface is defined by a backing roller there must therefore be means for allowing this second, backing, roller to move away from the first roller. In general, the elongated surface usually has a depression in it at a point distant from the nonreturn valve so as to permit the tube to have substantially its normal diameter despite contact with the roller.

The pump is portable and manually operable and for convenience the housing therefore has a pistol grip and the means for squeezing the tube and moving the roller are operable by operation of a member in or on the pistol grip. Conveniently this member is a trigger pivoted on the housing.

Normally the housing forms a solid outer casing, having an outlet for the tube if the tube is inside the housing, but it may merely be, for example, a framework carrying the tube and all the moving parts.

The preferred pump according to the invention has extreme simplicity of design and in it the elongated surface is an arcuate surface and the means for squeezing and moving the roller comprise a lever pivoted at the centre of curvature of the surface and one end of which, upon rotation about the pivot, causes the roller to move towards the non-return valve while squeezing the tube. Means for causing the lever to rotate about its pivot usually extend out of the housing. For example the second end of the lever may extend out of the housing and be directly operable by hand or, more usually, this end of the lever engages a trigger mounted on the housing in such a way that depression of the trigger causes rotation of the lever.

Other systems of achieving peristaltic pumping may be used but in general are less satisfactory since although they can usually be simpler than any known peristaltic pumps they are not usually quite as simple as the preferred system described, having an arcuate surface and lever. For example the smooth surface may be a flat surface and the roller may be caused to move along parallel with the surface, for example by passage between the surface and a parallel thrust plate. Movement of the roller in this way may be effected by, for example, a lever having a slot in which the roller is slideably and rotatably engaged. In another method the surface again does not have to be an arcuate surface and the lever can consist of two parts pivoted to one another, one part being pivoted on the housing and the roller being carried by the other part which is biased, for example by a spring, up against the tube. In fact this mechanism can conveniently be used also when the elongated surface is an arcuate surface and the lever is pivoted at a point that is not the centre of curvature of the surface.

It is often particularly important that air should not enter the tube and thus joints in the tube are kept to a minimum. Preferably the entire tube, i.e., both the flexible part and any non-flexible part, for example the part containing the non-return valve, should be moulded as a single piece.

The invention is illustrated in the accompanying drawings. In these:

FIG. 1 is a vertical cross section through one pump according to the invention,

FIG. 2 is a similar cross section through another pump according to the invention, and FIG. 3 is a side view of a pump connected up with a reservoir ready for use.

The pumps illustrated are all designed for use as a medical or veterinary syringe and thus are fitted with an injection needle.

Referring to FIG. 1, the pump comprises a portable housing 1 capable of being held in a user's hand having a pistol grip 2 and having a substantially smooth, arcuate, inside top surface 3. A flexible tube 4 enters the housing 1 through a circular inlet opening 5 and extends over the surface 3 from the inlet 5 towards and into an outlet 6 from the housing. This tube merges at its end near the outlet with an enlarged part of tube, shown as 7 in the drawing, that includes a non-return valve 7a. This valve is of conventional construction and is designed to allow liquid to flow through the tube at the outlet only in the direction from the back of the housing to the front of the housing, i.e., in the direction from the inlet 5 to the outlet 6. The tube finally terminates in a cylindrical fitting 8 over which a sleeve 9 carrying a needle 10 forms a tight and air-proof fit.

A roller 11 is rotatably mounted in one end of a member 12 that is pivoted at 13 about the end of an elongated member 14. The other end of the member 12 is biased by spring 15 downwards, as shown in the drawing, the roller 11 thus being biased upwards and against the tube 4. The member 14 is itself pivoted at point 16 on the housing and to which the spring 15 is secured. A coil spring 17 is fitted and serves to bias the member 14 to rotate to the position where point 13 is near the back of the housing.

A trigger 18 is mounted in the pistol grip part, 2, of the housing about a pivot 19. This trigger is U-section in form and the end of the member 14 distant from the point 13, labelled 20 in the drawing, is in slideable engagement with the inner surface of the front of the trigger 21, i.e., with the bottom of the U-section.

In FIG. 1 the roller is shown in the rest position, at its backwardmost point of travel, and at this position there is a shallow recess 22 in the smooth surface with the result that although the roller presses against the tube the tube is depressed into the depression 22 and so retains most at least of its original diameter.

Upon depressing the trigger 18 the inside surface of the front 21 of this trigger presses against the end 20 of the member 14 and causes the member to rotate in an anti-clockwise direction and this in turn causes the member 12 and the roller 11 to move from right to left. The spring 15 causes the roller to press against the tube sufficiently to seal it, the liquid thereby being pumped forward through the tube. Thus, in use, the operator holds the pump in his hand, inserts the needle 10 into the patient or animal, and presses the trigger, whereupon liquid is forced through the non-return valve and needle into the animal or patient. At the end of the desired injection stroke the trigger is released and the roller and the trigger return to their original position under the action of the spring 17. The non-return valve prevents entry of atmospheric air into the tube via the needle. Liquid in the rear section of the tube, outside the housing, can then enter the tube by passage between the roller and the depression 22.

One or more openings 23 may be provided in the trigger capable of receiving pegs that serve as stops to control the travel of the trigger, and thus the travel of the roller and thereby the amount of liquid ejected.

In FIG. 1 surface 3 is curved but pivot 16 is not necessarily at its centre of curvature, although it can be. Also it is not absolutely essential for the surface to be an arcuate surface in view of the presence of the member 12 and the spring 15.

The pump illustrated in FIG. 2 differs from that in FIG. 1 in that the members 12 and 14 are replaced by a single lever 24 in one end of which the roller 11 is rotatably mounted. In place of the coil spring 17 a helical spring 25 is provided to bias the lever and the roller to the rest position. The surface 3 is an arcuate surface and the pivot 16 is at the centre of curvature of the surface. Another minor modification is that the tube is moulded as an integral piece and the non-return valve, not shown, is thus included in a part 7 that is of the same diameter as the remainder of the tube.

In FIG. 3 is shown diagrammatically how the pump illustrated in FIG. 2 may conveniently be put into operation for injecting vaccine or other liquid into humans or living animals. In this drawing the tube 4 extends out of the back of the housing 1 through the opening 5 to a container 26. The tube extends through the seal 27 of the container, making a tight fit with the seal, to the bottom of the container. The container is formed of flexible plastic material so that as liquid is pumped out of it the walls of the container collapse.

The pump illustrated in FIGS. 1 or 2 can be modified in many ways. For example the tube can lay over the top surface of the housing and the lever 24 or the lever system 12 and 14 can extend out of the housing and press the roller down onto top surface of the housing.

I claim:

1. A peristaltic pump comprising a portable housing capable of being held in the hand and which carries means on an inner surface of the housing defining an elongated surface, a tube leading across the housing in contact with the inner surface of the housing defining an elongated surface and that includes, near one end of the housing, a non-return valve that allows fluid to flow only in the direction that leads away from the housing, the tube being a flexible tube along at least that part of its length in contact with the inner surface of the housing defining an elongated surface, a roller which is reciprocable along the flexible tube, means for squeezing the tube against the inner surface of the housing by a roller and thereby closing the tube and for moving the roller along the tube towards the non-return valve while thus squeezing the tube, means for continuously biasing the roller away from the non-return valve, and means to withdraw the roller from squeezing contact with said tube during or subsequent to its return to its initial position consisting of a depression in said inner surface of the housing defining an elongated surface at a point distant from the non-return valve, whereby the flexible tube returns substantially to its normal configuration while the non-return valve closes.

* * * * *